US006885785B2

(12) United States Patent
Dunphy et al.

(10) Patent No.: US 6,885,785 B2
(45) Date of Patent: Apr. 26, 2005

(54) OPTICAL FIBER BRAGG GRATING COATING REMOVAL DETECTION

(75) Inventors: James R. Dunphy, South Glastonbury, CT (US); James J. Ryan, Windsor Locks, CT (US)

(73) Assignee: United Technologies Corporation, Hartford, CT (US)

( * ) Notice: Subject to any disclaimer, the term of this patent is extended or adjusted under 35 U.S.C. 154(b) by 0 days.

(21) Appl. No.: 10/894,153

(22) Filed: Jul. 19, 2004

(65) Prior Publication Data

US 2005/0018945 A1 Jan. 27, 2005

Related U.S. Application Data

(62) Division of application No. 10/199,966, filed on Jul. 19, 2002, now abandoned, which is a continuation of application No. 08/346,059, filed on Nov. 29, 1994, now abandoned.

(51) Int. Cl.[7] .................................................. G02B 6/00
(52) U.S. Cl. ........................................ 385/12; 385/37
(58) Field of Search ............................. 385/12, 31, 33, 385/37

(56) References Cited

U.S. PATENT DOCUMENTS

| 3,570,449 A | 3/1971 | Blecherman et al. |
|---|---|---|
| 4,114,980 A | 9/1978 | Asam et al. |
| 4,245,883 A | 1/1981 | Johnson et al. |
| 4,390,589 A | 6/1983 | Geyling et al. |
| 4,468,294 A | 8/1984 | Hocker et al. |
| 4,725,110 A | 2/1988 | Glenn et al. |
| 4,761,073 A | 8/1988 | Meltz et al. |
| 5,003,600 A | 3/1991 | Deason et al. |
| 5,007,705 A | 4/1991 | Morey et al. |
| 5,020,379 A | 6/1991 | Berthold et al. |
| 5,321,257 A | 6/1994 | Danisch |
| 5,324,933 A | 6/1994 | Berkcan |
| 5,351,324 A | 9/1994 | Forman |
| 5,359,681 A | * 10/1994 | Jorgenson et al. ............ 385/12 |
| 5,361,130 A | * 11/1994 | Kersey et al. .............. 356/478 |
| 5,361,314 A | 11/1994 | Kopelman et al. |
| 5,394,488 A | * 2/1995 | Fernald et al. ................ 385/13 |
| 5,399,854 A | 3/1995 | Dunphy et al. |
| 5,400,522 A | 3/1995 | Kremer et al. |
| 5,401,956 A | 3/1995 | Dunphy et al. |
| 5,493,113 A | 2/1996 | Dunphy et al. |
| 6,144,026 A | 11/2000 | Udd et al. |

FOREIGN PATENT DOCUMENTS

| CA | 1149209 | 7/1983 |
|---|---|---|
| GB | 2196735 | 5/1988 |
| WO | WO8601303 | 2/1986 |

* cited by examiner

*Primary Examiner*—Akm Enayet Ullah
*Assistant Examiner*—Jennifer Doan
(74) *Attorney, Agent, or Firm*—Niro, Scavone, Haller & Niro

(57) ABSTRACT

An optical corrosion sensor employs an optical fiber Bragg grating 20 embedded within an optical fiber 18. The grating 20 has a coating 40 made of a material, such as aluminum, which corrodes or can otherwise be removed. The coating 40 exerts forces 46 radially inward around and along the grating 20 so as to cause the wavelength bandwidth of the grating reflectivity profile to become broader and to be shifted relative to its uncoated condition. Also, the forces on the grating 20 are reduced when the coating corrodes, thereby causing the wavelength bandwidth and shift of the reflectivity profile of the grating to narrow and to return to its uncoated condition.

21 Claims, 1 Drawing Sheet

OPTICAL FIBER BRAGG GRATING COATING REMOVAL DETECTION

CROSS REFERENCES TO RELATED APPLICATIONS

This is a division of U.S. patent application Ser. No. 10/199,966, flied on Jul. 19, 2002, now abandoned which is a continuation of U.S. patent application Ser. No. 08/346,059, filed on Nov. 29, 1994, now abandoned.

U.S. patent application Ser. No. 08/346,104, entitled "Highly Sensitive Optical Fiber Cavity Coating Removal Detection," which was filed contemporaneously with Application No. 08/346,059 on Nov. 29, 1994, and is now U.S. Pat. No. 5,493,113, issued Feb. 20, 1996, contains subject matter related to that disclosed herein.

TECHNICAL FIELD

This invention relates to smart structures and, more particularly, to optical corrosion detection.

BACKGROUND ART

It is known in the field of optical temperature and strain sensor technology to distribute sensors along a surface of or within a surface of a structure. Such sensors provide information about the stresses induced at various points on the structure, thereby providing information regarding fatigue, lifetime, and maintenance repair cycles of the structure. Such sensor-integrated structures and the optics that make them functional are known as "smart structures." One such system is described in U.S. Pat. No. 5,399,854, entitled "Embedded Optical Sensor Capable of Strain and Temperature Measurement Using a Single Diffraction Grating."

In addition to measuring stresses and temperatures at various points in a structure, it is also desirable to ascertain information regarding corrosion of structural components to determine when the structure is unfit for its normal use. For example, if corrosion occurs at critical stress points along the fuselage or wings of an airplane, structural failure may result.

Thus, it is desirable to obtain a sensor capable of detecting corrosion in structural materials.

DISCLOSURE OF INVENTION

Objects of the invention include provision of an optical sensor which detects corrosion.

According to the present invention an optical sensor, comprises an optical fiber; a fiber grating embedded within the fiber having a reflection wavelength bandwidth of a reflectivity profile for reflecting incident light; a coating of a material having a predetermined thickness and being around the perimeter and along the length of the fiber grating; the coating exerting forces radially inward around and along the grating so as to cause the wavelength bandwidth of the reflectivity profile of the grating to become broader than it would be without the coating; and the forces on the grating being reduced when the coating is at least partially removed, thereby causing the wavelength bandwidth of the reflectivity profile of the grating to narrow.

According further to the present invention, the forces from the coating also cause a peak reflection wavelength of the grating to exhibit a wavelength shift from a value that the peak reflection wavelength would be at without the coating and wherein the wavelength shift is reduced when the coating is at least partially removed.

According still further to the present invention, the coating comprises aluminum.

The invention represents an advancement in smart structure technology which allows for the detection of corrosion in structures by the discovery that a grating coated with a material, such as aluminum, causes the grating reflectivity profile to broaden and shift. The amount of broadening and shifting which occurs can be adjusted by the process chosen to apply the coating to the fiber grating sensor and the material the coating is made from. The invention is lightweight, inexpensive, and easy to install and has high sensitivity to corrosion. Furthermore, the sensor is easily coupled with other smart sensor technology such as temperature and/or strain sensors which also use fiber Bragg gratings.

The foregoing and other objects, features and advantages of the present invention will become more apparent in light of the following detailed description of exemplary embodiments thereof as illustrated in the accompanying drawings.

BEST MODE FOR CARRYING OUT THE INVENTION

Figure 1:
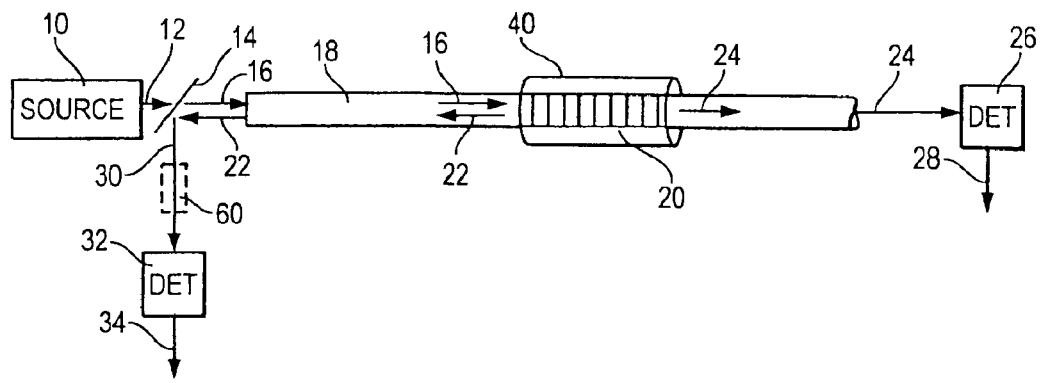
FIG. 1 is a diagram of a Bragg grating in an optical fiber which is coated with an aluminum coating, in accordance with the present invention.

Referring to FIG. 1, a light source 10 provides an optical signal 12 to a beam splitter 14 which passes a predetermined amount of light 16 into an optical fiber 18. The optical signal 16 is incident on a Bragg grating 20 which is impressed within the core of the optical fiber 18. A fiber Bragg grating, as is known, is a periodic refractive index variation which reflects a narrow wavelength band of light and passes all other wavelengths, thereby exhibiting a narrow wavelength reflectivity profile, as is discussed in U.S. Pat. No. 4,725,110 to Glenn et al.

A portion 22 of the light 16 is reflected off the grating 20, and the remaining wavelengths are passed through the grating 20 as indicated by the output light 24. The light 24 exits the fiber 18 and is incident on a detector 26, which provides an electrical signal on a line 28 indicative of the intensity of the light 24 incident thereon. Similarly, the reflected light 22 exits the fiber 18 and is incident on the beam splitter 14 which reflects a predetermined portion of the light 22, as indicated by a line 30, onto a detector 32. The detector 32 provides an electrical signal on a line 34 indicative of the intensity of the light 30 incident thereon. Also, the fiber grating 20 is surrounded by a coating 40 made of, e.g., aluminum (methods for coating are discussed hereinafter).

Figure 2:
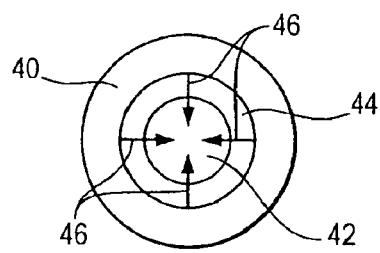
FIG. 2 is a cross-sectional view of an optical fiber Bragg grating showing a core, a cladding, and an aluminum coating, in accordance with the present invention.

Referring now to FIG. 2, a cross-sectional view of the fiber grating 20 includes a fiber core 42, made of germania-doped silica, having a diameter of about 6 to 9 microns. Surrounding the core 42 is a cladding 44 made of pure silica having an outer diameter of about 125 microns. Surrounding the cladding 44 is the outer coating 40 of aluminum having an outer diameter of about 196 microns. Other materials and diameters for the core, cladding, and coating may be used if desired.

Figure 3:
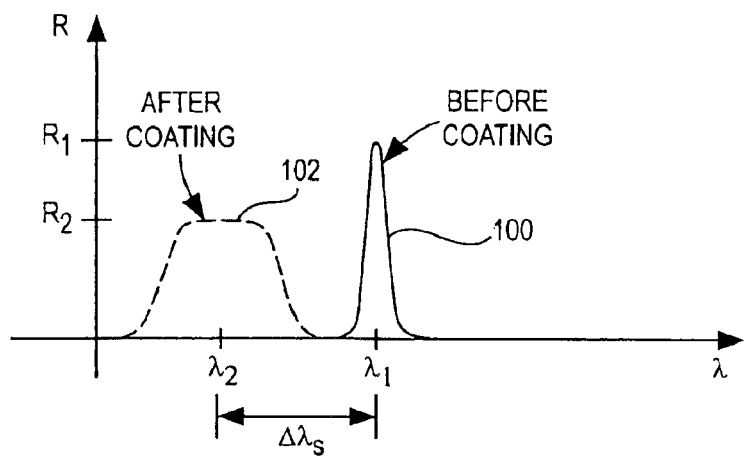
FIG. 3 is a graph showing the reflected optical spectrum of a Bragg grating before and after application of the coating of FIG. 1, in accordance with the present invention.

Referring now to FIG. 3, we have found that when a fiber grating is coated and placed into compression by a material such as aluminum, two effects occur to a normal narrow reflection (or reflectivity) profile 100 (or filter function) of a typical uncoated grating. First, the wavelength band of the reflectivity profile of the grating increases, i.e., becomes broader or wider, from the uncoated narrow grating profile 100 to the coated broadened grating profile 102. Second, the central reflection wavelength of the reflectivity profile shifts from $\lambda_1$ of the uncoated profile 100 to a shorter wavelength $\lambda_2$ of the coated profile 102, for a total wavelength shift of $\Delta\lambda s$.

The wavelength broadening effect is due to small non-uniform changes in the refractive index of the fiber caused by pressure or forces (also known as "microbends") exerted by the aluminum coating 40 on the cladding 44 and the core 42, as indicated by lines 46. Such small non-uniformities can occur naturally as grain boundaries when the aluminum is cooled on the surface of the glass fiber. Also, such non-uniformities are due to the fact that the coating 40 (FIG. 2) is not perfectly uniform around the circumference (or perimeter) of the cladding 44, and thus, pressure 46 exerted by the coating 40 is not uniformly applied. Furthermore, because the coating 40 is not perfectly uniform in thickness along the longitudinal axis or length of the grating 20 (FIG. 1), pressure 46 (FIG. 2) exerted on the grating 20 will randomly vary along the length of the grating 20, thereby also contributing to such non-uniformities. The coating therefore causes a random pressure gradient along the longitudinal axis of the grating 20 (and also circumferentially around the grating) which causes an associated random variation in refractive index. In particular, the microbends disrupt the smooth sinusoidal periodic refractive index variation which creates the narrow reflectivity profile of the typical narrow-band Bragg grating.

Such pressure gradient and the associated refractive index change can also reduce the reflection efficiency (i.e., the peak reflectivity) of the grating 20 from a reflectivity R1 for an uncoated grating to a lower reflectivity R2 for a coated grating due to the broadening of the wavelength reflectivity profile.

Also, the wavelength shift $\Delta\lambda s$ is caused by a change in the overall force exerted on the grating from that which exists in an uncoated grating. Thus, the greater the overall force exerted on the grating by the coating, the larger the wavelength shift $\Delta\lambda s$ will be.

As the coating 40 around the grating 20 corrodes, pressure exerted by the coating 40 is reduced, thereby reducing the magnitude of the microbends as well as the overall average force on the grating. As such, when the coating is completely removed the grating returns to its normal narrow reflectivity profile as indicated by the curve 100 in FIG. 3, having a central reflection wavelength of $\lambda_1$. If the coating is only partially removed, i.e., the coating is merely thinned or is removed only in some areas but not others, a corresponding change toward the uncoated grating reflectivity profile will result. The amount of coating removal needed before the grating will exhibit a change in the grating reflectivity profile depends on the initial force applied to the grating by the coating, the stiffness of coating material, and the thickness of the coating remaining, and can be easily determined by those skilled in the art.

As discussed hereinbefore, we have found that the wavelength shift $\Delta\lambda s$ is due to an overall average force exerted by the coating on the grating and the bandwidth increase is caused by the aforementioned microbends (or non-uniform forces applied to the grating). As a result, we have found that the process used for coating the grating and the type of coating material used, determines the amount of wavelength shift $\Delta\lambda s$ and the amount of narrowing of the reflectivity profile which occurs.

Accordingly, if the fiber is coated with aluminum when the fiber is at the melting temperature of aluminum, e.g., by dipping the fiber into molten aluminum at temperature of about 650° C. then removing the fiber to facilitate cooling and adhesion of the coating to the surface of the fiber, the large difference in thermal expansion coefficients between fiber and aluminum cause a large overall force to be exerted on the fiber during cooling. This technique is known as "freeze coating." In that case, the average wavelength shift $\Delta\lambda s$ may be of the order of −4.9 nm due to the compressive strain effect of the aluminum along the length and around the circumference of the optical fiber after cooling occurs. Also, the increase in the reflection bandwidth of the grating (e.g., the full-width-half-max. value) for this technique may be about a factor of 3 or less, e.g., an effective increase from about 0.17 nm to 0.55 nm or less.

However, if the fiber is maintained substantially at ambient temperature during the coating process (e.g., by sputtering or by vapor deposition), the cooling temperature gradient for the fiber is not as large and, thus, the overall average force exerted on the fiber is not as large as the previously discussed dipping technique. Accordingly, the wavelength shift $\Delta\lambda s$ is smaller. Also, when using such a process, the coating tends to be quite smooth and uniform. As such, the non-uniform forces or microbends are less and, thus, the change in reflection bandwidth is less, than the aforementioned dipping technique.

Therefore, we have found that it is possible to tailor the amount of reflection wavelength shift by adjusting the amount of overall average force applied to the grating which is directly related to the temperature of the fiber during coating and the thermal expansion coefficient of the coating material. Also, we have found that it is possible to tailor the amount of reflection bandwidth broadening by adjusting the smoothness and uniformity of the coating applied to the grating.

It should be understood that the source 10 may be a broadband light source and the detector 32 may be an optical spectrometer which provides an electrical signal 34 indicative of the wavelength reflectivity profile, i.e., the reflected wavelengths and the associated intensities thereof. Alternatively, the source 10 may be a variable source such as used in an active wavelength scan/interrogation technique, such as that disclosed in U.S. Pat. No. 5,401,956, entitled "Diagnostic System for Fiber Grating Sensors."

Any other means of analyzing the optical output signals 30 or 24 (depending on whether the device is operating in reflection or transmission) may be used to detect the changes in the optical output signals due to corrosion. However, the sensing technique is not critical to the present invention. For example, an optional fiber grating 60, which is matched to the reflectivity profile of the grating 20 without a coating, may be placed between the detector 32 and the beamsplitter 14, in the path of the light 30 and the grating 20 coated with the technique discussed hereinbefore that minimizes wavelength shift. In that case, when the grating 20 is coated (and the reflectivity profile is broad), the reflected light 22 and 30 will also be broadband. Also, because the grating 60 has a narrower reflectivity profile than the incident light 30, a portion of the light 30 will pass through the grating 60 and be seen at the detector 32. Conversely, when the coating is removed from the grating 20, the reflectivity profiles of the two gratings 20, 60 match and no (or minimal) light is passed to the detector 32.

Alternatively, the two gratings 20, 60 may be matched and coated, with only the grating 20 being exposed to corrosion. In that case, light will be minimized when no corrosion exists and, when the coating on the grating 20 corrodes, the light seen by the detector will be maximized due to the higher reflectivity of the uncoated fiber.

Also, it should be understood that either or both of the effects of removal of the coating from the grating, i.e., the change in width of the reflectivity profile and/or the central wavelength shift, may be used to detect corrosion.

Furthermore, a material other than aluminum may be used as the coating around the grating, provided such coating either corrodes, evaporates, thins, or in some other way is removed partially of completely from coating the grating so as to reduce the forces exerted on the grating. Therefore, the invention may be used to detect the partial or complete removal of any coating surrounding a grating, provided a predetermined criteria of changes in overall average force and non-uniformity of forces on the grating are satisfied, as discussed hereinbefore.

Also, instead of applying the coating to the entire length of the grating, a portion of the grating length may be coated.

Although the invention has been described and illustrated with respect to the exemplary embodiments thereof, it should be understood by those skilled in the art that the foregoing and various other changes, omissions and additions may be made without departing from the spirit and scope of the invention.

We claim:

1. An optical sensor comprising:
   an optical fiber;
   a fiber grating embedded within said optical fiber, said grating having a reflection wavelength bandwidth of a reflectivity profile for reflecting incident light;
   a coating of a material having a predetermined thickness and being around the circumference and along the length of said fiber grating, said coating exerting forces radially inward around and along said grating so as to cause said wavelength bandwidth of said reflectivity profile of said grating to become broader than it would be without said coating, wherein said forces on said grating are reduced when said coating is at least partially removed, thereby causing the wavelength bandwidth of said reflectivity profile of said grating to narrow which provides an optical parameter for sensing removal of said coating; and
   a detector for sensing removal of said coating by utilizing said optical parameter to detect narrowing of the wavelength bandwidth of said reflectivity profile of said grating.

2. The sensor of claim 1 wherein said optical fiber comprises a fiber core and a cladding surrounding said fiber core.

3. The sensor of claim 1 wherein said forces from said coating are non-uniformly distributed around and along said grating and disrupt a periodic reflective index variation of said grating, thereby causing the broadening of said wavelength bandwidth of said reflectivity profile.

4. The sensor of claim 1 wherein said forces from said coating also cause a peak reflection wavelength of said grating to exhibit a wavelength shift from a value that said peak reflection wavelength would be at without said coating and wherein said wavelength is reduced when said coating is at least partially removed.

5. The sensor of claim 4 wherein said forces from said coating exert an overall average force around and along said grating thereby causing said wavelength shift.

6. The sensor of claim 1 wherein said coating comprises aluminum.

7. The sensor of claim 1 wherein the removal of said coating comprises corrosion of said coating.

8. The sensor of claim 1 wherein said detector comprises an optical spectrometer for providing an electrical signal indicative of the wavelengths and intensities of light passing through or reflected from said fiber grating.

9. The sensor of claim 8 wherein said detector further comprises at least one of (i) a broadband light source and (ii) a variable light source for actively scanning/interrogating the wavelength bandwidth of said reflectivity profile.

10. The sensor of claim 1 wherein said detector comprises a second fiber grating for filtering said light passing through or reflected from said fiber grating.

11. A method of making an optical sensor, the method comprising:
    obtaining an optical fiber with a fiber grating embedded therein;
    applying a coating to said fiber grating around the circumference of and along the length of said grating;
    said coating being applied to said grating such that coating exerts non-uniform forces around and along said grating, said forces causing a wavelength bandwidth of a reflectivity profile of said grating to become broader than it would be without said coating, wherein said forces on said grating are reduced when said coating is at least partially removed, thereby causing the wavelength bandwidth of said reflectivity profile of said grating to narrow which provides an optical parameter for sensing removal of said coating; and
    providing a detector for sensing removal of said coating by utilizing said optical parameter to detect narrowing of the wavelength bandwidth of said reflectivity proflle of said grating.

12. The method of claim 11, wherein:
    said coating exerts an overall average force around and along said grating thereby causing a peak reflection wavelength of said grating to exhibit a wavelength shift from a value that said peak reflection wavelength would be at without said coating; and
    said wavelength is reduced when said coating is at least partially removed.

13. The method of claim 11, wherein said coating comprises aluminum.

14. The method of claim 11, wherein said step of applying said coating comprises vapor deposition.

15. The method of claim 11, wherein said step of applying said coating comprises freeze coating.

16. The method of claim 11 wherein removal of said coating comprises corrosion of said coating.

17. A method of detecting corrosion, the method comprising:
    providing an optical fiber having an embedded fiber grating with a corrodible coating that exerts forces on said grating so as to cause a wavelength bandwidth of a reflectivity profile of said grating to become broader than it would be without said coating; and
    sensing removal of said coating by detecting narrowing of the wavelength bandwidth of said reflectivity profile as said coating corrodes.

18. The method of claim 17 wherein said optical fiber comprises a fiber core and a cladding surrounding said fiber core.

19. The method of claim 17 further comprising the step of associating said optical fiber with a structure to enable detection of corrosion of said structure by sensing said removal of said coating.

20. The method of claim 19, wherein said structure is part of an aircraft.

21. The method of claim 17 wherein said coating has a predetermined thickness and predetermined mechanical properties, said thickness and mechanical properties being selected so that corrosion of said coating will cause a detectible reduction in the wavelength bandwidth in accordance with the amount of said coating removed by said corrosion.

* * * * *